United States Patent
Eldeab et al.

(10) Patent No.: US 11,066,371 B2
(45) Date of Patent: Jul. 20, 2021

(54) PYRIDINE COMPOUND, MAKING, AND USE THEREOF

(71) Applicants: Hany Abdel Aziz Eldeab, Al-Ain (AE); Yaser E. Greish, Al-Ain (AE); Sneha Thomas, Al-Ain (AE); Sherif M. Karam, Al-Ain (AE)

(72) Inventors: Hany Abdel Aziz Eldeab, Al-Ain (AE); Yaser E. Greish, Al-Ain (AE); Sneha Thomas, Al-Ain (AE); Sherif M. Karam, Al-Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 16/067,709

(22) PCT Filed: Dec. 29, 2016

(86) PCT No.: PCT/IB2016/058085
§ 371 (c)(1),
(2) Date: Jul. 2, 2018

(87) PCT Pub. No.: WO2017/115321
PCT Pub. Date: Jul. 6, 2017

(65) Prior Publication Data
US 2019/0010127 A1 Jan. 10, 2019

Related U.S. Application Data

(60) Provisional application No. 62/273,238, filed on Dec. 30, 2015.

(51) Int. Cl.
*C07D 213/85* (2006.01)
*C07D 409/04* (2006.01)
*A61P 1/00* (2006.01)

(52) U.S. Cl.
CPC .............. *C07D 213/85* (2013.01); *A61P 1/00* (2018.01); *C07D 409/04* (2013.01)

(58) Field of Classification Search
CPC .................................................. C07D 213/85
USPC ....................................................... 534/560
See application file for complete search history.

(56) References Cited

U.S. PATENT DOCUMENTS 9,051,271 B2  6/2015  Abdou et al.

OTHER PUBLICATIONS

Gaffer et al., J. Appli. Sci. &. Res. (2013) vol. 9(6), pp. 4051-4058.*
Shi et al., Nano Lett. (2010) vol. 10(9), pp. 3223-3230.*
Sheng-Nan et al., Chin. Phys. B (2014) vol. 23(3), pp. 037503-1 to 037503-19.*
King, Med. Chem. Principle and Practice (1994) pp. 206-208.*
Abdellattiff, M. H. et al. "Efficient Microwave-Assisted Solvent-Free synthesis and Molecular Docking Studies of 2-pyridone derivatives as Anticancer Agents and Evaluation of Cytotoxic Effects", Journal of Advances in Chemistry, 2016, 12(4), 4351-4364.
Abdou, I. M. et al. "Fast and efficient microwave synthetic methods for some new 2(1H)-pyridone arabinosides", Heterocyclic communications, 2012, 18(3), 135-141.
Attia, A. M. E. et al. "Nucleic acid related compounds: A convenient synthesis of 3-deazauridine analogues", Nucleosides & Nucleotides, 1995, 14(6), 1211-1218.
Elgemeie, G. E. H. et al. "Convenient Synthesis of 2(1H)-Pyridinethione Glycosides", Bulletin of the Chemical Society of Japan, 1994, 67, 1627-1632.
Elgemeie, G. E. H. et al. "Reaction of (Cyano)thioacetamide with arylhydrazones of β-Diketones: Novel Synthesis of 2(1H)-pyridinethiones, Thieno[2,3-b]pyridines, and Pyrazolo[3,4-b]pyridines", Bulletin of the Chemical Society of Japan, 1993, 66, 555-561.
Helal, M. H. et al. "Synthesis of new 5-arylazo-3-cyano-4,6-dimethyl-2-acetylchloridethiopyridine reactive disperse dyes and their applications in textile printing", Pigment and Resin Technology, 2008, 37(4), 234-242.
Rateb, N. M. et al. "Antimicrobial evaluation of new synthesized pyridine nucleosides under solvent-free conditions", Nucleosides, Nucleotides and Nucleic Acids, 2013, 32, 493-509.
Schmidt, U. et al. "Syntheses with the thioamides of malonic acid. III. Syntheses in the adermine series. 1. Conversions of cyanothiopyridones to cyanopyridines by oxidation and reduction", Chemische Berichte, 1960, 93, 1590-1597 & CAPLUS Accession No. 1960:128947.
International Search Report issued in corresponding International Application No. PCT/IB2016/058085, dated Mar. 6, 2017, Australian Patent Office, Woden Act, Australia.

* cited by examiner

*Primary Examiner* — Taofiq A Solola
(74) *Attorney, Agent, or Firm* — Hauptman Ham, LLP

(57) ABSTRACT

The present disclosure provides a substituted pyridine derivative, which can be used as a bioactive compound for inhibiting stomach cell lines and/or inducing regeneration of damaged stomach lining.

19 Claims, 5 Drawing Sheets

PYRIDINE COMPOUND, MAKING, AND USE THEREOF

CROSS-REFERENCE TO RELATED APPLICATIONS

This application claims priority benefit to U.S. Provisional Application No. 62/273,238, filed Dec. 30, 2015, which is hereby incorporated herein by reference in its entirety.

TECHNICAL FIELD

The present disclosure relates to a substituted pyridine compound, optionally immobilized on a magnetic nanoparticle such as those comprising iron and methods for making both. Although subject to multiple uses, in some embodiments, the substituted pyridine compound and immobilized product thereof is usable for inhibiting growth of stomach stem cells and, therefore, is useful in the treatment of stomach cancer.

INTRODUCTION

Current cancer research seeks development of biologically active anticancer drugs with low toxicity. Pyridine is one of the most important heterocyclic aromatic compounds and there is great interest in the synthesis of pyridine and related derivatives for applications in industry.

SUMMARY

In one aspect, provided is a substituted pyridine derivative selected from compounds of formula (I)

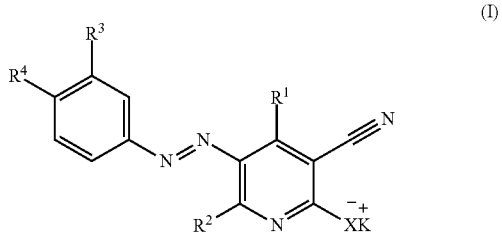

(I)

pharmaceutically acceptable salts, hydrates, and solvates thereof,
wherein:
$R^1$ is selected from $C_1$-$C_6$ alkyl, $C_3$-$C_5$ cycloalkyl, and $C_1$-$C_6$ haloalkyl;
$R^2$ is selected from $C_1$-$C_6$ alkyl, 5-membered heterocyclyl, and phenyl;
$R^3$ is selected from H, $C_1$-$C_6$ alkyl, $C_3$-$C_5$ cycloalkyl, $C_1$-$C_6$ alkoxy, halo, $NO_2$, $NH_2$, OH, CN, haloalkyl, $SO_3H$, $SO_2NH_2$, COOH and $CONH_2$;
$R^4$ is selected from H, $C_1$-$C_6$ alkyl, $C_3$-$C_5$ cycloalkyl, $C_1$-$C_6$ alkoxy, halo, $NO_2$, $NH_2$, OH, CN, $C_1$-$C_6$ haloalkyl, $SO_3H$, $SO_2NH_2$, COOH and $CONH_2$; and
X is O or S.

In another aspect, provided is the substituted pyridine derivative immobilized on a surface of an optionally coated magnetic nanoparticle.

In another aspect, provided is a scaffold comprising the substituted pyridine derivative immobilized on the surface of the optionally coated magnetic nanoparticle. In one embodiment, the scaffold is a microfibrous biodegradable polymeric scaffold.

In another aspect, provided is methodology for treating damaged gastric wall, comprising inducing differentiation of gastric stem cells into gastric functional cells.

In another aspect, provided is methodology for regenerating gastric lining, comprising inducing differentiation of gastric stem cells into gastric functional cells.

In another aspect, provided is methodology for treating gastric carcinoma, comprising inducing differentiation of gastric stem cells into gastric functional cells.

DETAILED DESCRIPTION

Figure 1:
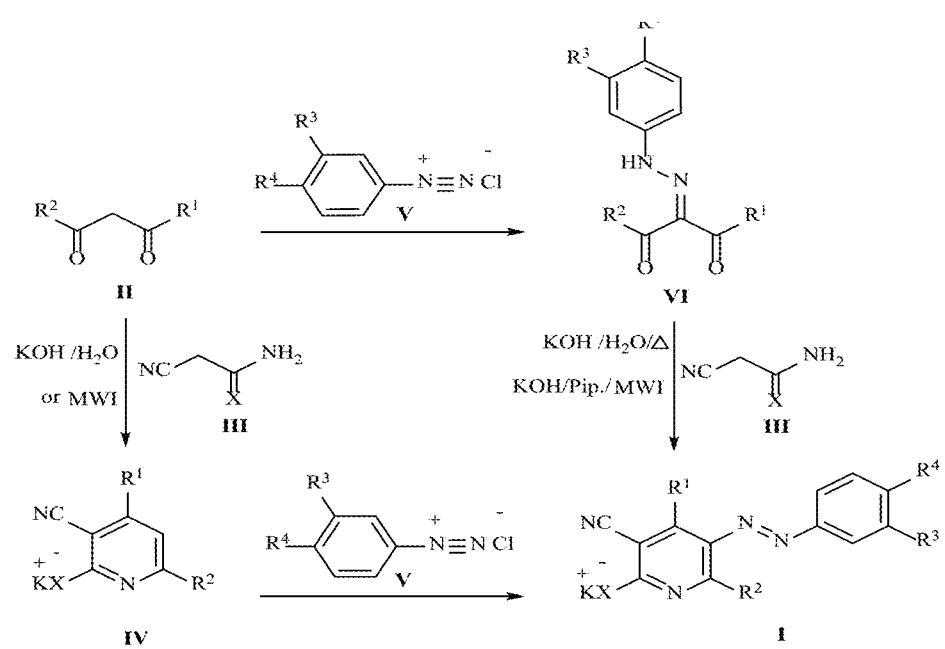
FIG. 1: Schema illustrating clean chemical synthesis of potassium (E)-3-cyano-4-methyl-5-((4-nitrophenyl)diazenyl)-6-phenylpyridin-2-olate (I).

The term "alkyl" as used herein alone or as part of another group refers to a straight or branched chain aliphatic hydrocarbon chain, having from 1 to 6 carbon atoms. Examples of alkyl include, but are not limited to methyl, ethyl, n-propyl, isopropyl, n-butyl, n-pentyl, t-butyl and the like. Alkyl groups may further be substituted with one or more suitable substituents.

The term "alkoxy" covers "alkyl-O—" wherein alkyl is as defined above. Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), and the like.

The term "cycloalkyl" refers to cyclic alkyl groups constituting of 3 to 5 carbon atoms having a single cyclic ring. Such cycloalkyl groups include, by way of example, single ring structures, for example, cyclopropyl, cyclobutyl, cyclopentyl, and the like. Cycloalkyl groups may further be substituted with one or more suitable substituents.

The term "heterocyclyl" unless otherwise specified refers to a monocyclic compound, fully or partially unsaturated, constituting of 5 ring-member atoms, one or more carbon atoms, and one or more heteroatom(s) independently selected from N, O, S or P. The nitrogen, sulphur and phosphorus heteroatoms may optionally be oxidized. The nitrogen atoms may optionally be quaternerized. The heterocyclyl group may be further substituted at any available position with one or more suitable substituents. Examples of heterocyclyl groups include but are not limited to, thienyls (such as thien-2-yl), furyls (such as fur-3-yl), pyrrolyls (such as pyrrol-3-yl), 2H-Pyrrolyls (such as 2H-Pyrrol-3-yl), imidazolyls (such as imidazol-2-yl), pyrazolyls (such as pyrazol-1-yl), isothiazolyls (such as isothiazol-3-yl), isoxazolyls (such as isoxazol-3-yl), 1,3-thiazolyls, and the like. The heterocyclyl groups may be further substituted with one or more suitable substituents.

The "phenyl" groups may optionally be further substituted with one or more suitable substituents.

Suitable substituents for the phenyl, heterocycyl, cycloalkyl, alkoxy, and alkyl groups may independently be optionally made at any available position by one or more substituents independently selected from $C_{1-6}$ alkyl, $C_3$-$C_6$ cycloalkyl, phenyl, heterocycyl, —F, —Cl, —Br, and —I. For example, in some embodiments, the suitable substituents may be optionally made at any available position by from one, two, three four, five, or six substituents independently selected from those noted above. For another example, in some embodiment, the suitable substituents are made at each available atom of the group. In some embodiments, substituents are not further substituted.

The term "halo" as used herein refers to —F, —Cl, —Br, and —I.

The term "haloalkyl" as used herein alone or as part of another group refers to a straight or branched chain aliphatic hydrocarbon chain, having from 1 to 6 carbon atoms in which one or more hydrogen atoms are replaced with a halo. For another example, in some embodiment, the suitable halo substituents are made for each available hydrogen atom of the group, e.g., "perfluoro-", "perchloro-", "perbromo-", or "periodo-" substitutions (such as perhalomethyl, like —$CF_3$). In some embodiments, the suitable halo substituents are different and made for each available hydrogen atom of the group. In some embodiments, the suitable halo substituents are the same or different and made for less than all the available hydrogen atoms of the alkyl group.

The term "nanoparticles" refers to a structure that has at least one physical dimension of approximately 1-100 nanometers. In some embodiments, the structure has an aspect ratio approaching 1. In some embodiments, the aspect ratio is greater than 1.2 or ranges from 2-4. In some embodiments, the nanoparticles have a $D_{50}$ ranging from 10-100 nm or 30-80 nm.

Current cancer research seeks development of biologically active anticancer drugs with low toxicity. Pyridine is one of the most important heterocyclic aromatic compounds and there is great interest in the synthesis of pyridine and related derivatives for applications. In recent years, research has considered magnetite nanoparticles for various uses, including MRI-contrast agents and drug delivery vehicles.

The present inventors synthesized novel substituted pyridine derivatives, which can be used as a bioactive compound for inhibiting stomach cell lines and/or inducing regeneration of damaged stomach lining. For example, such novel substituted pyridine derivatives can be used as bioactive compounds on the surface of magnetite particles, wherein such magnetite particles can be used as a drug delivery vehicle to the stomach for inducing differentiation of gastric stem cells into gastric functional cells. The substituted pyridine derivatives, optionally on the surface of magnetite particles, may be administered to a human in need thereof in an effective amount. Such administration may be varied so as to inhibit stomach cell line and/or induce regeneration of damaged stomach lining and includes oral administration to the human in need thereof, e.g., to treat stomach cancer. In so differentiating, the substituted pyridine derivatives can induce the regeneration of damaged stomach lining due to stomach carcinoma or stomach ulcer.

The present inventors developed compositions, methodology, and the like for synthesizing novel potassium pyridinium salts that inhibit stomach stem cell growth.

Substituted Pyridine Derivative
A. Chemical Structures and Synthesis of Novel Substituted Pyridine Derivative The present disclosure relates to a substituted pyridine derivative selected from compounds of formula (I)

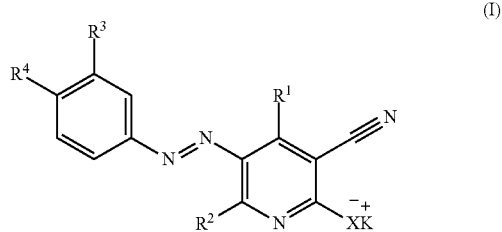

pharmaceutically acceptable salts, hydrates, and solvates thereof,
wherein:
$R^1$ is selected from $C_1$-$C_6$ alkyl, $C_3$-$C_5$ cycloalkyl, and $C_1$-$C_6$ haloalkyl;
$R^2$ is selected from $C_1$-$C_6$ alkyl, 5-membered heterocyclyl, and phenyl;
$R^3$ and $R^4$ are independently selected from H, $C_1$-$C_6$ alkyl, $C_3$-$C_5$ cycloalkyl, $C_1$-$C_6$ alkoxy, halo, $NO_2$, $NH_2$, OH, CN, haloalkyl, $SO_3H$, $SO_2NH_2$, COOH and $CONH_2$;
X is O or S.

In some embodiments, the substituted pyridine derivative is selected from those in which:
$R^1$ is selected from $C_1$-$C_6$ alkyl and $CF_3$;
$R^2$ is selected from $C_1$-$C_6$ alkyl, 5-membered heterocyclyl, and phenyl;
$R^3$ and $R^4$ are independently selected from H, $C_1$-$C_6$ alkyl, $C_1$-$C_6$ alkoxy, halo, $NO_2$, $NH_2$, OH, CN, $C_1$-$C_6$ haloalkyl, $SO_3H$, $SO_2NH_2$, COOH and $CONH_2$;
X is O or S.

In some embodiments, the substituted pyridine derivative is selected from those in which:
$R^1$ is selected from $C_1$-$C_3$ alkyl and $C_3$ cycloalkyl, and $C_1$-$C_3$ haloalkyl;
$R^2$ is selected from thien-2-yl and phenyl;
$R^3$ is selected from $NO_2$, $SO_3H$, $SO_2NH_2$, COOH and $CONH_2$;
$R^4$ is selected from H, $C_1$-$C_3$ alkyl, $NO_2$; and
X is O or S.

In some embodiments, the substituted pyridine derivative is selected from those in which:
$R^1$ is selected from $C_1$ alkyl and —$CF_3$;
$R^2$ is selected from thien-2-yl and phenyl;
$R^3$ is selected from $NO_2$, $SO_3H$, $SO_2NH_2$, COOH and $CONH_2$;
$R^4$ is selected from H, $C_1$ alkyl, $NO_2$; and
X is O or S.

In some embodiments, $R^1$ is selected from $C_1$-$C_6$ alkyl and $CF_3$. In some embodiments, $R^1$ is selected from —$CH_3$ and —$CF_3$.

In some embodiments, $R^2$ is selected from $C_1$-$C_6$ alkyl, 5-membered heterocyclyl, and phenyl. In some embodiments, $R^2$ is selected from thien-2-yl and phenyl.

In some embodiments, $R^3$ is selected from H, $C_1$-$C_6$ alkyl, halo, $NO_2$, $NH_2$, OH, CN, $C_1$-$C_6$ haloalkyl, $SO_3H$, $SO_2NH_2$, COOH and $CONH_2$. In some embodiments, $R^3$ is selected from $NO_2$, $SO_3H$, $SO_2NH_2$, COOH and $CONH_2$.

In some embodiments, $R^4$ is selected from H, $C_1$-$C_6$ alkyl, halo, $NO_2$, $NH_2$, OH, CN, $C_1$-$C_6$ haloalkyl, $SO_3H$, $SO_2NH_2$, COOH and $CONH_2$. In some embodiments, $R^4$ is selected from H, $C_1$ alkyl, $NO_2$.

In some embodiments, $R^3$ and $R^4$ are the same. In some, $R^3$ and $R^4$ are different.

In some embodiments, $R^1$, $R^2$, $R^3$ and $R^4$ are selected from groups that are substituted. In some embodiments, $R^1$, $R^2$, $R^3$ and $R^4$ are selected from groups that are unsubstituted. In some embodiments, some $R^1$, $R^2$, $R^3$ and $R^4$ are selected from groups that are substituted while the remainder are unsubstituted.

In some embodiments, X is O. In some embodiments, X is S.

Clean Chemical Synthesis of New Substituted Pyridinium Salts (I):

A variety of different modified derivatives of the potassium pyridinium salt (I) were synthesized using classical approaches in aqueous solution. The present disclosure contemplates a direct method to synthesize the target potassium pyridinium salts (I). Two different clean synthetic strategies were used to prepare the azo pyridinium salts (I) as shown in FIG. 1. Pyridium salts (IV) obtained from the condensation of unsaturated ketone (II) with cyanocetamide or cyanothioacetamide (III) under eco-friendly heating using water or other solvent or microwave assisted heating. Coupling of arenediazonium chlorides (V) with the produced pyridium salt (IV) afforded the corresponding azo pyridinium salts (I).

In the second strategy, conventional methodology used a mixture of cyanocetamide or cyanothioacetamide (III), and the corresponding 2-arylhydrazono-1,3-di substituted-propane-1,3-dione (VI) in water containing potassium hydroxide. The reaction mixture was promoted to heat for 1 hour and the product was isolated in a crystalline form in 61% yields. A new one-pot microwave synthetic protocol was used to obtain the same target compounds (I) using base catalyst without solvent in an excellent yield (96%).

FIG. 1 provides an illustrative and non-limiting clean chemical synthesis of the pyridine derivatives, such as potassium (E)-3-cyano-4-methyl-5-((4-nitrophenyl)diazenyl)-6-phenylpyridin-2-olate (I).

Table 1 below provides examples of the pyridine derivatives, such as derivatives of potassium (E)-3-cyano-4-methyl-5-((4-nitrophenyl)diazenyl)-6-phenylpyridin-2-olate (I). $I_a I_q$ are each examples of the pyridine derivatives.

TABLE 1

| Compound No. | X | $R_1$ | $R_2$ | $R_3$ | $R_4$ |
|---|---|---|---|---|---|
| $I_a$ | O | $CH_3$ | $C_6H_5$ | H | $CONH_2$ |
| $I_b$ | O | $CH_3$ | $C_6H_5$ | H | COOH |
| $I_c$ | O | $CH_3$ | $C_6H_5$ | H | $NO_2$ |
| $I_d$ | O | $CH_3$ | $C_6H_5$ | $NO_2$ | $NO_2$ |
| $I_e$ | O | $CH_3$ | $C_6H_5$ | H | $SO_3H$ |
| $I_f$ | O | $CH_3$ | $C_6H_5$ | H | $SO_2NH_2$ |
| $I_g$ | O | $CH_3$ | $C_6H_5$ | $SO_2NH_2$ | H |
| $I_h$ | O | $CF_3$ | $C_6H_5$ | H | $NO_2$ |
| $I_l$ | O | $CF_3$ | $C_6H_5$ | H | $SO_3H$ |
| $I_m$ | O | $CF_3$ | 2-thienyl | H | $NO_2$ |
| $I_n$ | O | $CF_3$ | 2-thienyl | H | $SO_3H$ |
| $I_o$ | S | $CH_3$ | $C_6H_5$ | H | COOH |
| $I_p$ | S | $CH_3$ | $C_6H_5$ | H | $NO_2$ |
| $I_q$ | S | $CH_3$ | $C_6H_5$ | H | $SO_3H$ |

Figure 2:
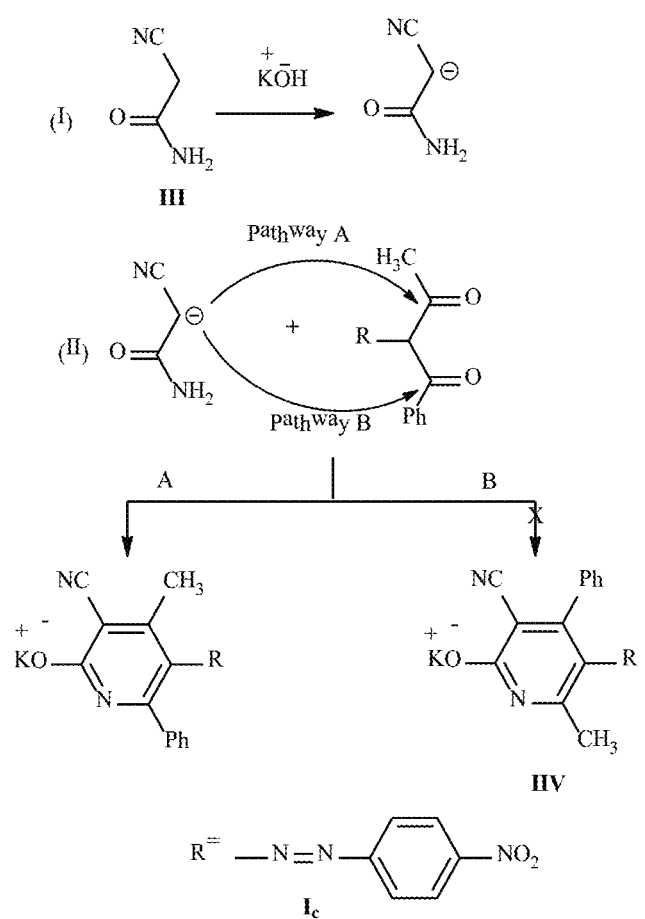
FIG. 2: Mechanistic pathway for the clean synthesis of potassium (E)-3-cyano-4-methyl-5-((4-nitrophenyl)diazenyl)-6-phenylpyridin-2-olate ($I_c$)

The structure of the obtained products I was clearly confirmed on the basis of their elemental analyses and spectral data (LC-MS/MS, IR, UV, 1D- and 2D-NMR). Thus, model compound IC revealed a molecular formula $C_{19}H_{13}KN_5O_3$. LC-MS (ionization method): m/z 398 (M). The formation of $I_C$ was proven using IR which revealed the appearance of the carbonitrile group appeared at v 2225 $cm^{-1}$. UV-vis absorption spectrum of $I_C$ showed two characteristic absorption bands corresponding to n→π* and π→π* electronic transitions. The weak absorption band n→π* at λ=277 nm and the high absorbance band π-π* at λ=384 nm is found, indicating the formation of trans isomer by the symmetry rules. The $^1$H-NMR spectrum of compound $I_C$ showed a single peak at δ=2.65 ppm corresponding to the methyl protons at C-4. Aromatic protons appeared at δ=7.35-8.21 ppm as multiplets. $^{13}$C-NMR (100 MHz, DMSO-$d_6$) showed the appearance of signal corresponding to the $CH_3$ at δ=21.7 ppm. Another peak at δ=119.4 ppm assigned for the nitrile carbon atom (C≡N). Signals appeared at δ=99.5 ppm and δ=170.3 ppm corresponding to the pyridine C-3 and C-2, respectively. 2D-NMR was used to confirm the suggested structures and the data obtained from 2D-NMR strongly agreed with the mechanistic pathway. However, this reaction can proceed through the formation of two isomers, 6-phenyl 2-pyridines $I_C$ or 4-phenyl 2-pyridines VI isomer. The only product isolated from the reaction is 3-cyano-4-methyl-6-phenyl-5-(4'-Chlorophenylazo)-2-pyridone $I_C$ (FIG. 2). The structure of the obtained isomer $I_C$ was confirmed using 2D-NMR technique.

Figure 3:
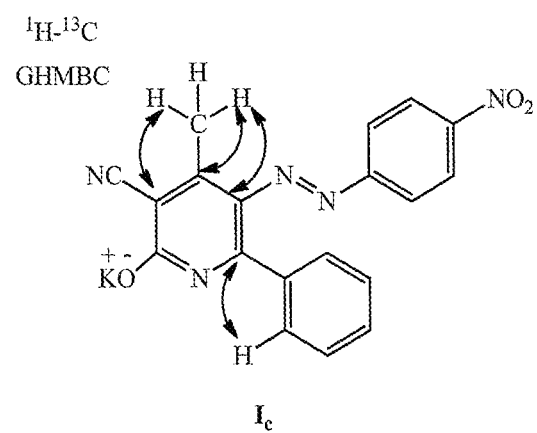
FIG. 3: 2D-gHMBC spectrum of compound $I_c$.
Figure 3:
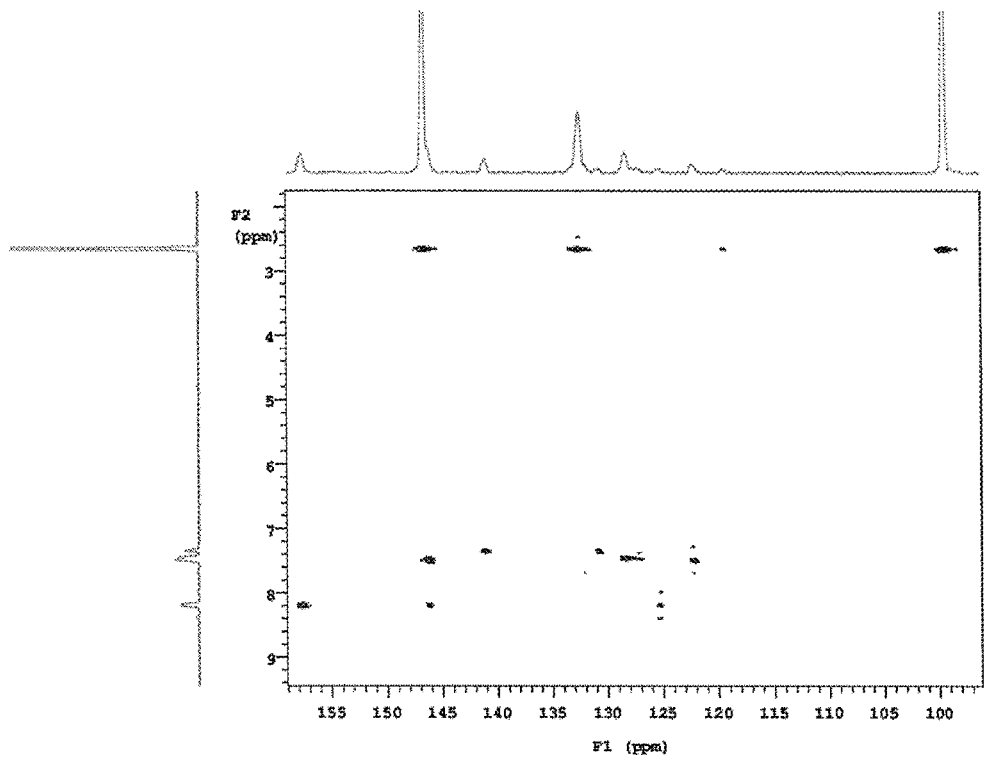
Figure 4:
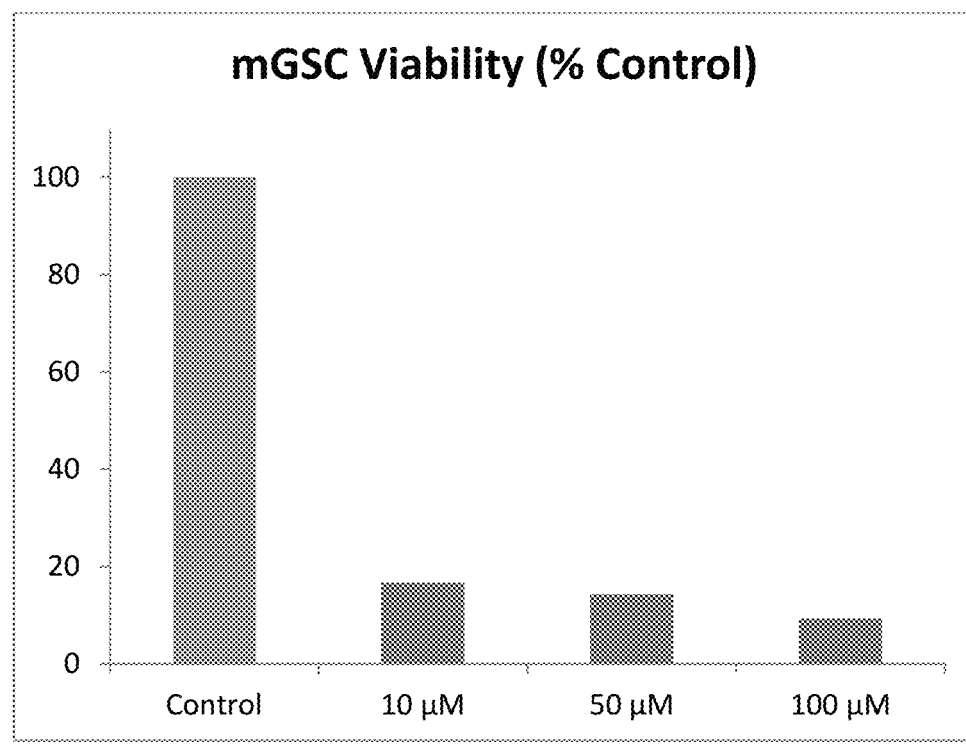
FIG. 4: mGSC Viability (% Control).

$^1$H-$^{13}$C chemical shift (gHMBC) (FIG. 3) showed clear structure elucidation, whereas methyl protons (δ=2.68 ppm) at pyridine C-4 showed strong cross-peak interactions with pyridine C-4 (δ=146.7 ppm) and C-3 (δ=99.5 ppm). Another cross-peak interaction between methyl protons at pyridine C-4 (δ=2.68 ppm) and pyridine C-5 (δ=132.6 ppm) was observed. While a weak cross-peak interaction between methyl protons at pyridine C-4 (δ=2.68 ppm) and the carbonitrile carbon (δ=119.4 ppm). On the other hand phenyl protons at pyridine C-6 (δ=7.43-8.21) and pyridine C-5 (δ=132.6 ppm) was observed. The $^1$H-$^{13}$C correlation showed no cross peak interactions between phenyl protons (δ=7.43-8.21 ppm) at pyridine C-6 and the pyridine C-4 (δ=146.7 ppm), C-3 (δ=99.5 ppm) or the carbonitrile carbon (δ=119.4 ppm) supporting the formation of Potassium (E)-3-cyano-4-methyl-5-((4-nitrophenyl)diazenyl)-6-phenylpyridin-2-olate ($I_c$) as single isomer not Potassium (E)-3-cyano-6-methyl-5-((4-nitrophenyl)diazenyl)-4-phenylpyridin-2-olate (IIV) as shown in FIG. 2.

B. Complexing Novel Substituted Pyridine Derivative(s) on Surface of Magnetite Particle The present disclosure also relates to a substituted pyridine derivative, as described herein, immobilized on the surface of an optionally coated magnetic nanoparticle. In some embodiments, the substituted pyridine derivative is immobilized.

In some embodiments, the magnetic nanoparticles comprise one or more metal selected from iron, nickel, or cobalt. In some embodiments, the magnetic nanoparticles comprise magnetite ($FeO_4$) or maghemite ($\gamma$-$Fe_2O_3$).

In some embodiments, the magnetic nanoparticles are coated. In some embodiments, the coating comprises chitosan.

In some embodiments, the magnetic nanoparticles are selected from magnetite ($FeO_4$) or maghemite ($\gamma$-$Fe_2O_3$) coated with chitosan, which has free amino or hydroxyl groups to facilitate binding to the pyridine derivate.

A novel substituted pyridine derivative can be immobilized on a magnetite surface. For example, magnetite ($Fe_3O_4$) nanoparticles (NPs, ≤100 nm) will be used as vehicles for the delivery of the novel substituted pyridine derivatives. Magnetite NPs will be prepared in a basic medium (pH=13) using $Fe^{2+}$ and $Fe^{3+}$ sources, in the presence of chitosan, which is a known biodegradable polymer. Magnetite NPs coated with a thin chitosan layer will be centrifuged, washed with deionized water 3-5 times before being suspended in a phosphate buffer solution (PBS). An approximately 10 ml suspension of chitosan-coated magnetite NPs will be blended with an equal volume of an aqueous solution containing various concentrations of each of the pyridine derivatives. The mixture will be thoroughly mixed for 12 hours, then centrifuged and washed 3-5 times. The remaining pellet will be dried in a vacuum oven then investigated for its structure using infrared spectroscopy (IR), and thermogravimetric analysis (TGA) and for its morphology using transmission electron microscopy (TEM) and energy dispersive x-ray (EDX) spectroscopy. Upon confirmation of the coating composition and morphology, optimization of the concentration of the immobilized pyridine derivative will be carried out based on the required dose to be delivered.

C. Delivering Novel Substituted Pyridine Derivative(s) on Surface of Magnetite Particle An instant magnetite particle can be delivered/administered to a patient in need, targeting stomach cancer region. For instance, delivery of the novel substituted pyridine compounds will take place through the slow degradation of the chitosan layer carrying it and the subsequent release of the pyridine compound. The magnetic properties of the magnetite nanoparticles will enable the physicians to track the pathway of the administered coated nanoparticles using magnetic resonance imaging (MRI).

EXAMPLES

The following examples concern particular embodiments and do not in any way limit the scope or spirit of the present disclosure. A person of ordinary skill in the art may use the present disclosure and examples to make equivalent embodiments which, though not expressly stated, perform the same or similar functions to attain the same or similar results, and therefore are encompassed by the scope and spirit of the present disclosure.

Example 1: Experimental "Materials and Methods"

Equipment and Materials Used:

Microwave synthesis was performed using CEM Microwave system. Melting points were determined on (Pyrex capillary) Gallenkamp apparatus. Infrared spectra were recorded with a Thermo Nicolet Nexus 470 FT-IR spectrometer in the range 4000-400 $cm^{-1}$ using potassium bromide disks. The ultraviolet absorption spectra, in the region 200-600 nm were recorded using a Secoman Anthelie 2 Advanced spectrophotometer in 1.00 cm cells at 25° C. The spectra were run in spectraquality methanol using concentration of $5 \times 10^{-5}$ M. $^1$H-NMR spectra, APT, DEPT, $^{13}$C-NMR spectra were obtained on Varian Gemini 400 and 200 MHz FT NMR spectrometer in $CDCl_3$ and DMSO-$d_6$; chemical shifts were recorded in δ(ppm) units, relative to $Me_4Si$ as an internal standard. The mass spectra were recorded on Shimadzu LCMS-QP 800 LC-MS and AB-4000 Q-trap LC-MS/MS. Analytical data were obtained using PerkinElmer 2400 II series CHN Analyzer. Thin-layer chromatography (TLC) was carried out on precoated Merck silica gel $F_{254}$ plates and UV light was used for visualization. Column chromatography was performed on a Merck silica gel. The reagents were purchased from Aldrich and used without further purification.

Example 2: Clean Chemical Synthesis of Potassium (E)-3-Cyano-4-Methyl-6-Phenylpyridin-2-Olate ($I_C$)

A mixture of equimolar amounts of the substituted acetone (II) and cyanoacetamide or cyanothioacetamide (III) (5 mmol) was suspended in water (5 mL) containing potassium hydroxide (7 mmol). The reaction mixture was irradiated at 200 W for 2-3 min in a 10 mL closed vial using CEM Microwave system or heated for 1 hour. After completion of the reaction, as indicated by TLC, the water was completely evaporated and the resulting solid product was collected and washed with cold water to remove sodium chloride then dried to afford the product (IV).

Example 3: Synthesis of Potassium (E)-3-Cyano-4-Methyl-5-((4-Nitrophenyl)Diazenyl)-6-Phenylpyridin-2-Olate ($I_C$)

Sodium acetate (3.0 g) was added to a solution of the corresponding pyridium salt (IV) (0.01 mol) in 30 ml of ethanol. The mixture was cooled to 0° C. for 10 min then cooled solution of arenediazonium chloride (V) (prepared from 0.01 mol of the corresponding aromatic amine and the appropriate quantities of HCl and $NaNO_2$) was added with stirring. The reaction mixture was stirred for an additional one hour after which the solid component was collected, washed with 2×10 ml of water and 2×10 ml of ethanol, and dried in the air to afford potassium pyridinium salt (I).

Example 4: Characterizing Data for the Synthesized Compound $I_C$ $I_C$: Potassium (E)-3-cyano-4-methyl-5-((4-nitrophenyl)diazenyl)-6-phenylpyridin-2-olate mp>300° C.; IR (KBr, cm-1) 2225 (CN), $^1$H-NMR (400 MHz, DMSO-$d_6$) δ 2.65 (s, 3H, $CH_3$), 7.35-7.45 (m, 5H, Ar—H), 7.65-7.68 (d, 2H, Ar—H, J=9.2 Hz), 8.19-8.21 (d, 2H, Ar—H, J=9.2 Hz); $^{13}$C-NMR (400 MHz, DMSO-$d_6$) δ 21.7 ($CH_3$), 99.5 (C-3), 116.8 (C-6), 117.1 (C-3'), 117.5 (C-5'), 119.4 (CN), 122.2 (C-4''), 125.3 (C-2''), 127.3 (C-6''), 128.4 (C-3''), 129.1 (C-5''), 130.7 (C-2'), 132.6 (C-5), 141.1 (C-1''), 146.2 (C-6'), 146.7 (C-4), 157.7 (C-1'), 167.4 (C-4'); 170.3 (C-2), LC-MS (ionization method): m/z 398 (M); Anal. Calcd for $C_{19}H_{13}KN_5O_3$: C, 57.27; H, 3.29; N, 17.58. Found: C, 57.11; H, 3.34; N, 17.60.

Example 5: Complexing Novel Substituted Pyridine Derivative(S) on Surface of Magnetite Particle A novel substituted pyridine derivative can be immobilized on a magnetite surface. For example, magnetite ($Fe_3O_4$) nanoparticles (NPs, ≤100 nm) will be used as vehicles for the delivery of the novel substituted pyridine derivatives. Magnetite NPs will be prepared in a basic medium (pH=13) using $Fe^{2+}$ and $Fe^{3+}$ sources, in the presence of chitosan, which is a known biodegradable polymer. Magnetite NPs coated with a thin chitosan layer will be centrifuged, washed with deionized water 3-5 times before being suspended in a phosphate buffer solution (PBS). An approximately 10 ml suspension of chitosan-coated magnetite NPs will be blended with an equal volume of an aqueous solution containing various concentrations of each of the pyridine derivatives. The mixture will be thoroughly mixed for 12 hours, then centrifuged and washed 3-5 times. The remaining pellet will be dried in a vacuum oven then investigated for its structure using infrared spectroscopy (IR), and thermogravimetric analysis (TGA) and for its morphology using transmission electron microscopy (TEM) and energy dispersive x-ray (EDX) spectroscopy. Upon confirmation of the coating composition and morphology, optimization of the concentration of the immobilized pyridine derivative will be carried out based on the required dose to be delivered.

Example 6: Delivering Novel Substituted Pyridine Derivative(S) on Surface of Magnetite Particle Delivery of the novel substituted pyridine compounds will take place through the slow degradation of the chitosan layer carrying it and the subsequent release of the pyridine compound. The magnetic properties of the magnetite NPs will enable the physicians to track the pathway of the administered coated nanoparticles using magnetic resonance imaging (MRI).

Example 7: Scaffold Comprising a Substituted Pyridine Derivative Immobilized on a Surface of a Magnetic Nanoparticle A solution containing 4 wt % of biodegradable chitosan in acetic acid will be processed into a non-woven micro- and nanofibrous scaffold using an electrospinning technique. These scaffolds have been shown to enhance the proliferation and differentiation of gastric stem cells in vitro. In order to immobilize the pyridine derivative onto the surfaces of these fibres, the pyridine derivative of various concentrations will be dissolved in the chitosan/acetic acid until a homogeneous solution is obtained. This solution will be electrospun into fibrous scaffolds using an electrospinning technique. The dried scaffolds will be loaded with gastric stem cells at a pre-calculated seeding density and will be soaked in a tissue culture media for up to 12 days. Differentiated gastric stem cells within the fibrous scaffolds will be used as a modality to replace defective gastric mucosal tissue.

Example 8: Novel Substituted Pyridine Derivative Induces Inhibition of mGS Cell Proliferation Novel substituted pyridine derivative induces inhibition of mouse gastric stem (mGS) cell proliferation.
Cell Culture and Viability Assay:

Two different cell lines, mouse gastric stem (mGS) cells were maintained in RBMI 1640 media obtained from Sigma, St Louis, USA. The culture media were supplemented with 50 I.U./mL penicillin, 50 µg/mL streptomycin, and 10% fetal bovine serum. Cells were seeded on 96-well plates at a density of 2,000 cells/well and maintained in humidified CO2 incubator at 37° C. After 24 hours, cells were treated with 5, 10, and 50 µM of the test compound in quadruplicates. Control cells were treated with equal volume of the vehicle (0.1% DMSO). The effects of the pyridine compound on mGS cells was examined 48 hours after treatment by using microscopy and MTT cell viability assay.

Microscopic examination of treated mGS cells revealed neither detached nor floating (no apoptotic) cells in the culture media. However, the number of attached mGS cells was much less than those of control untreated cells. For MTT assay, the yellow tetrazolium MTT (3-(4,5-dimethyl-thiazolyl-2)-2,5-diphenyltetrazolium bromide) was added to the cells. By the action of dehydrogenase enzymes in viable cells, the resulting intracellular purple formazan was solubilized and quantified by spectrophotometer. The data are presented as a % change in viability from the control untreated cells which are considered as 100%. The results showed a remarkable decrease in the number of treated mGS cells as compared to control. Therefore, results of both microscopic and biochemical studies suggest that the compound induced an inhibition of mGS cell proliferation.

Example 9: Novel Substituted Pyridine Derivative does not Affect Normal Cells

To test whether any of the instant novel substituted pyridine derivatives affect the viability of normal, healthy cells, dental pulp stem cells (DPSC) were tested. Briefly, DPSC were isolated from freshly extracted incisor of a normal rat.

Figure 5:
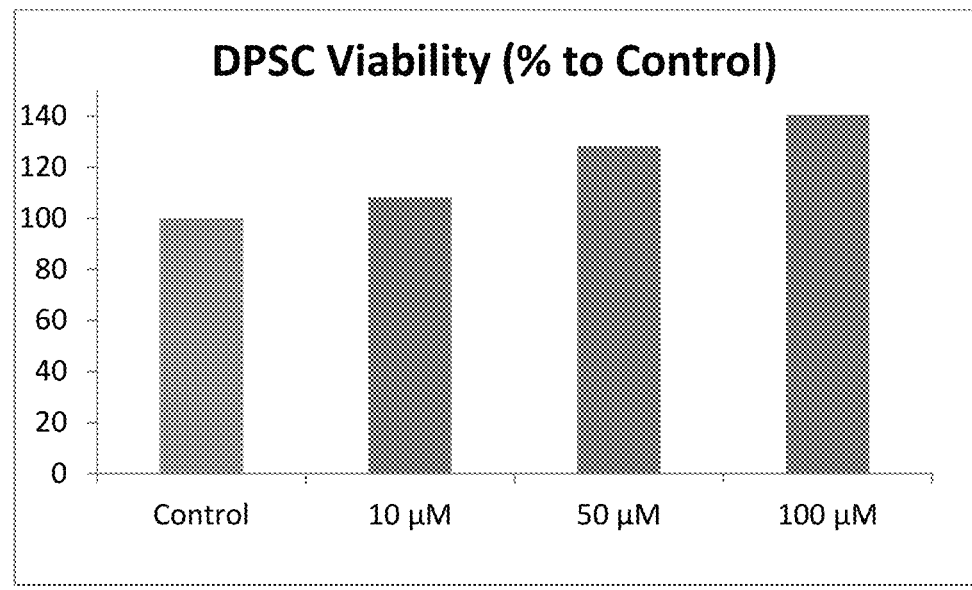
FIG. 5: Dental pulp stem cells (DPSC) were treated with 10, 50 and 100 μM of the compound in quadruplicates. After 48 hours, the cells were examined microscopically and the MTT cell viability assay was carried out to quantify the percent of viable cells as compared to control untreated cells. The histological results revealed no detectable difference between the morphology and amount of treated and control cells. Using the MTT assay, the compound seems to have no inhibitory effect on the proliferation of normal cells.

Microscopic examination revealed no detectable difference between the morphology and amount of treated and control cells. By using the MTT assay, the compound appeared to have no inhibitory effect on DPSC proliferation as shown in FIG. 5.

What is claimed is:
1. A method for treating a damaged gastric wall of a human, comprising exposing gastric stem cells to an effective amount of a substituted pyridine derivative selected from compounds of formula (I)

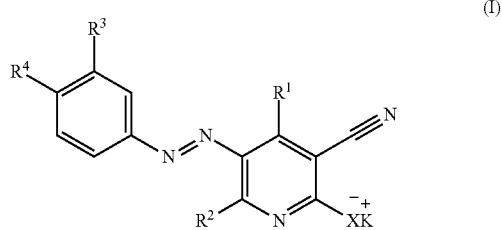

wherein:
R$^1$ is selected from the group consisting of C$_1$-C$_6$ alkyl, C$_3$-C$_5$ cycloalkyl, and C$_1$-C$_6$ haloalkyl;
R$^2$ is selected from the group consisting of C$_1$-C$_6$ alkyl, 5-membered heterocyclyl, and phenyl;
R$^3$ and R$^4$ are independently selected from the group consisting of H, C$_1$-C$_6$ alkyl, C$_3$-C$_5$ cycloalkyl, C$_1$-C$_6$ alkoxy, halo, NO$_2$, NH$_2$, OH, CN, haloalkyl, SO$_3$H, SO$_2$NH$_2$, COOH, and CONH$_2$;
X is S or O;
thereby inducing differentiation of the gastric stem cells into gastric functional cells.
2. The method for treating a damaged gastric wall of a human according to claim 1, wherein:
R$^1$ is selected from the group consisting of C$_1$-C$_6$ alkyl and CF$_3$;
R$^2$ is selected from the group consisting of C$_1$-C$_6$ alkyl, 5-membered heterocyclyl, and phenyl;
R$^3$ and R$^4$ are independently selected from the group consisting of H, C$_1$-C$_6$ alkyl, C$_1$-C$_6$ alkoxy, halo, NO$_2$, NH$_2$, OH, CN, C$_1$-C$_6$ haloalkyl, SO$_3$H, SO$_2$NH$_2$, COOH, and CONH$_2$; and
X is selected from the group consisting of O and S.
3. The method for treating a damaged gastric wall of a human according to claim 1, wherein:
R$^1$ is selected from the group consisting of C$_1$-C$_3$ alkyl and C$_3$ cycloalkyl, and C$_1$-C$_3$ haloalkyl;
R$^2$ is selected from the group consisting of thien-2-yl and phenyl;

$R^3$ is selected from the group consisting of $NO_2$, $SO_3H$, $SO_2NH_2$, COOH, and $CONH_2$;
$R^4$ is selected from the group consisting of H, $C_1$-$C_3$ alkyl, and $NO_2$; and
X is selected from the group consisting of O and S.

4. The method for treating a damaged gastric wall of a human according to claim 1, wherein:
$R^1$ is selected from the group consisting of Ci alkyl and $CF_3$;
$R^2$ is selected from the group consisting of thien-2-yl and phenyl;
$R^3$ is selected from the group consisting of $NO_2$, $SO_3H$, $SO_2NH_2$, COOH, and $CONH_2$;
$R^4$ is selected from the group consisting of H, Ci alkyl, and $NO_2$; and
X is S.

5. The method for treating a damaged gastric wall of a human according to claim 1, wherein $R^1$ is selected from the group consisting of $C_1$-$C_6$ alkyl and $CF_3$.

6. The method for treating a damaged gastric wall of a human according to claim 1, wherein $R^2$ is selected from the group consisting of $C_1$-$C_6$ alkyl, 5-membered heterocyclyl, and phenyl.

7. The method for treating a damaged gastric wall of a human according to claim 1, wherein $R^2$ is selected from the group consisting of thien-2-yl and phenyl.

8. The method for treating a damaged gastric wall of a human according to claim 1, wherein $R^3$ is selected from the group consisting of H, $C_1$-$C_6$ alkyl, halo, $NO_2$, $NH_2$, OH, CN, $C_1$-$C_6$ haloalkyl, $SO_3H$, $SO_2NH_2$, COOH, and $CONH_2$.

9. The method for treating a damaged gastric wall of a human according to claim 1, wherein $R^3$ is selected from the group consisting of $NO_2$, $SO_3H$, $SO_2NH_2$, COOH, and $CONH_2$.

10. The method for treating a damaged gastric wall of a human according to claim 1, wherein $R^4$ is selected from the group consisting of H, $C_1$-$C_6$ alkyl, halo, $NO_2$, $NH_2$, OH, CN, $C_1$-$C_6$ haloalkyl, $SO_3H$, $SO_2NH_2$, COOH, and $CONH_2$.

11. The method for treating a damaged gastric wall of a human according to claim 1, wherein $R^4$ is selected from the group consisting of H, $C_1$ alkyl, and $NO_2$.

12. The method for treating a damaged gastric wall of a human according to claim 1, wherein X is O.

13. The method for treating a damaged gastric wall of a human according to claim 1, wherein X is S.

14. A method for treating a damaged gastric wall of a human, comprising exposing gastric stem cells to an effective amount of a substituted pyridine derivative in which the pyridine derivative is immobilized on a surface of a magnetic nanoparticle, wherein the substituted pyridine derivative selected from compounds of formula (I)

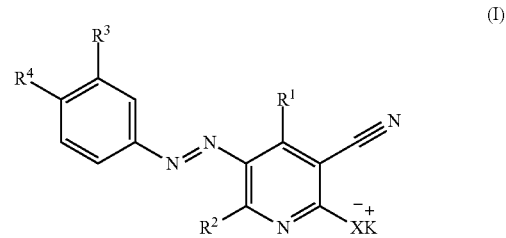

(I)

wherein:
$R^1$ is selected from the group consisting of $C_1$-$C_6$ alkyl, $C_3$-$C_5$ cycloalkyl, and $C_1$-$C_6$ haloalkyl;
$R^2$ is selected from the group consisting of $C_1$-$C_6$ alkyl, 5-membered heterocyclyl, and phenyl;
$R^3$ and $R^4$ are independently selected from the group consisting of H, $C_1$-$C_6$ alkyl, $C_3$-$C_5$ cycloalkyl, $C_1$-$C_6$ alkoxy, halo, $NO_2$, $NH_2$, OH, CN, haloalkyl, $SO_3H$, $SO_2NH_2$, COOH, and $CONH_2$; and
X is S.

15. The method for treating a damaged gastric wall of a human according to claim 14, further comprising a coating on a surface of the magnetic nanoparticles.

16. The method for treating a damaged gastric wall of a human according to claim 14, wherein the magnetic nanoparticles further comprise particles of magnetite ($FeO_4$) or maghemite ($\gamma$-$Fe_2O_3$).

17. The method for treating a damaged gastric wall of a human according to claim 14, further comprising a on a surface of a magnetic nanoparticle, wherein the substituted pyridine derivative is incorporated into the scaffold.

18. The method of claim 1, wherein the treating comprises regenerating gastric lining.

19. The method of claim 1, wherein the treating comprises treating gastric carcinoma, comprising inducing differentiation of gastric stem cells into gastric functional cells.

* * * * *